(12) United States Patent
Tylke

(10) Patent No.: US 7,438,717 B2
(45) Date of Patent: Oct. 21, 2008

(54) ANESTHESIA INTUBATING FORCEPS

(76) Inventor: James Tylke, 8517 SE. Merritt Way, Jupiter, FL (US) 33458

( * ) Notice: Subject to any disclaimer, the term of this patent is extended or adjusted under 35 U.S.C. 154(b) by 206 days.

(21) Appl. No.: 10/911,214

(22) Filed: Aug. 4, 2004

(65) Prior Publication Data

US 2006/0030880 A1    Feb. 9, 2006

(51) Int. Cl.
*A61B 17/28* (2006.01)
*A61M 25/01* (2006.01)

(52) U.S. Cl. .................. 606/108; 600/434; 606/207; 606/205

(58) Field of Classification Search ......... 606/205–211, 606/139, 144, 145, 148, 151, 153, 51, 52, 606/106, 119, 120, 157, 158; 600/434, 104, 600/141, 142, 562; D24/143; D8/52, 54; 30/29, 120, 131, 145, 194–204, 231, 232, 30/235, 257; 433/159; 81/119, 176.3, 418
See application file for complete search history.

(56) References Cited

U.S. PATENT DOCUMENTS

| 943,263 | A | | 12/1909 | Moraweck |
| 1,193,987 | A | | 8/1916 | Burdin |
| 3,316,913 | A | * | 5/1967 | Swenson ..................... 606/108 |
| 3,866,610 | A | * | 2/1975 | Kletschka ................... 606/208 |
| 4,552,143 | A | | 11/1985 | Lottick |
| 4,827,929 | A | * | 5/1989 | Hodge ........................ 606/139 |
| 5,476,479 | A | | 12/1995 | Green et al. |
| 5,591,203 | A | * | 1/1997 | Fahy .......................... 606/207 |
| 5,797,919 | A | | 8/1998 | Brinson |
| 5,997,566 | A | * | 12/1999 | Tobin ......................... 606/205 |
| 6,371,973 | B1 | | 4/2002 | Tepper |
| 2002/0077649 | A1 | * | 6/2002 | Lasner ........................ 606/174 |

FOREIGN PATENT DOCUMENTS

FR    002694179 A1    2/1994

* cited by examiner

*Primary Examiner*—Todd E Manahan
*Assistant Examiner*—Kathleen Sonnett
(74) *Attorney, Agent, or Firm*—Kevin P. Crosby; Daniel C. Crilly; Brinkley, Morgan et al.

(57) ABSTRACT

Forceps with a pair of scissor-like arms that are pivotally connected to each other and that continue past the pivot to form a catheter guide. At least two and preferably three bends are disposed in the arms immediately before the pivot, which allow the medical professional to place the guiding end of the forceps in the correct place while maintaining good visual contact with the patient's vocal cords. An alternative embodiment provides a fourth bend near the guiding end of the forceps that allows for easier insertion of a catheter in some patients, such as children.

11 Claims, 10 Drawing Sheets

ANESTHESIA INTUBATING FORCEPS

FIELD OF THE INVENTION

The present invention relates generally to medical equipment. More particularly, the present invention relates to intubation aides, such as forceps, used to guide tubes during insertion into a patient's body.

BACKGROUND OF THE INVENTION

Medical professionals have used various tools and implements in their treatment of patients, both human and animal, since the beginning of the profession. (For ease of reference, patients hereinafter will be discussed as human patients. It is understood that the invention described herein could be used on any animal.) Various procedures involve insertion of a catheter into a patient, including oral or nasal endotracheal intubation, during which a medical professional inserts a nasal or oral endotracheal tube into the patient's trachea to assist with the patient's ventilation.

In order to assist with endotracheal intubation, an implement, such as forceps, is used by the medical professional to guide and/or direct the catheter into the proper place. Another implement, called a laryngoscope, is used during nasal and oral endotracheal intubation to secure the patient's tongue and lift the mandible, i.e. jaw, to expose the vocal cords. When the patient's head is tilted back, as is done during the intubation procedure, and the tongue and jaw are stabilized and properly secured, the medical professional performing the intubation will have an unobstructed view of the patient's vocal cords, provided there are no foreign objects or fluids in the patient's mouth. However, when the medical professional inserts any of the currently-available guiding forceps into the patient's mouth, the medical professional's view is severely obstructed by his or her hand and by the forceps. Also, the currently-available forceps do not grasp and control the tube adequately. This makes the process of endoctracheal intubation more difficult and more time-consuming, which could mean the difference between life and death for a patient that requires assistance with ventilation.

One example of currently-available forceps is described in U.S. Pat. No. 3,316,913 to Swenson. The Swenson patent discloses locking catheter-guiding forceps that have a slight bend in the handles. When closed, the ends of the forceps define opposed gripping surfaces that are used to guide insertion of a catheter. The angle of the bend in the handles makes using the forceps disclosed in the Swenson patent difficult because the medical professional's hand will block his or her view into the patient's body.

U.S. Pat. No. 4,552,143 to Lottick, U.S. Pat. No. 5,797,919 to Brinson, U.S. Pat. No. 5,591,203 to Fahy, and U.S. Pat. No. 5,476,479 to Green all disclose medical implements that have an end that, when the implements' handles are closed, define a circular opening through which various items can be passed. These implements are all lacking, however, in that they do not allow the medical professional to have clear view and access to difficult areas to reach in a patient's body, such as during nasal or oral endotracheal intubation.

In endotracheal intubation situations, a key problem with many currently-available medical forceps is that the medical professional is required to grip or grab the nasally or orally-inserted catheter tube in the back of the pharynx and try to place the tube through the patient's vocal cords by frequently gripping and re-gripping the lubricated catheter tube, which is also coated with nasal and oral secretions and possibly blood in a traumatic situation. These forceps frequently have serrated edges or teeth, which assist in gripping the catheter tube but also can snag or catch on the soft tissues inside the patient's mouth and throat and damage the patient's vocal cords. Even if the patient is not harmed, these sharp edges on the forceps can rupture the balloon on the lower end of the catheter, which must be inflated once the catheter is inserted past the patient's vocal cords to create an air-tight seal and allow for ventilation.

Therefore, there exists a need to provide catheter-guiding forceps that allow a medical professional to have easy access to difficult-to-reach areas of a patient's body, such as in an oral or nasal endotracheal intubation, while simultaneously allowing the medical professional to have an unobstructed or virtually unobstructed view of the area in the patient's body in which the medical professional is working, such as the patient's vocal cords. Further, there exists a need to provide forceps that allow a catheter tube to easily pass through the forceps instead of requiring frequent re-gripping of the slippery catheter tube.

SUMMARY OF THE INVENTION

Generally, the present invention comprises forceps with a pair of scissor-like handles that are pivotally connected to each other and that continue past the pivot to form a pair of arms. There are at least two key bends in the handles immediately before the pivot, which allow the medical professional to place the distal, guiding end of the forceps in the correct place within the pharynx while simultaneously permitting good visual contact with the area of concern, particularly the patient's vocal cords, because the medical professional's hand holding the forceps is not in his or her line of sight of the area through which the tube is to be placed while using the forceps. During endotracheal intubation, the medical professional places the forceps into the area of the patient's oropharynx (i.e., the back of the throat). Then, the catheter tube can be guided through the forceps and past the patient's vocal cords through the glottis (i.e., the aperture through the vocal cords), where ventilation is maintained. The medical professional does not have to grip and re-grip the catheter tube during this process, eliminating the risk of harm to the patient and damage to the catheter tube that re-gripping may cause. Further, this invention does not have sharp edges or ridges to catch or snag either the patient's tissue or the balloon-like portion associated with the catheter tube.

DETAILED DESCRIPTION OF THE INVENTION

Figure 1:
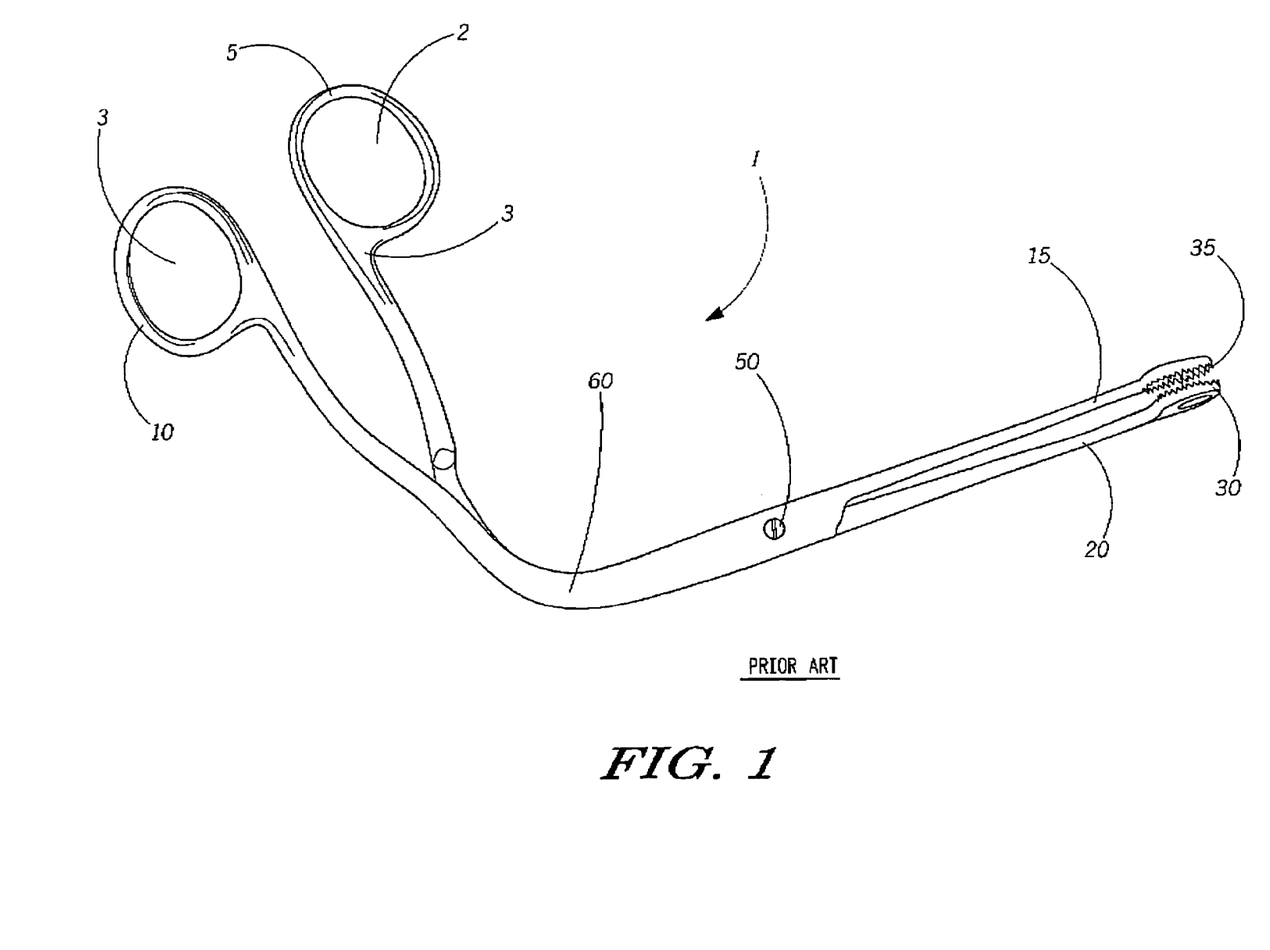
FIG. 1 is a left side elevational view of a prior art medical implement.

A catheter guiding device 1 that currently exists in the art is depicted in FIG. 1. A pair of handles 5, 10 each defines an aperture 2, 3 for a user to insert a finger and thumb. The handles 5, 10 are integrally connected to a pair of arms 15, 20. The handle 5 and arm 15 is pivotally connected to the handle 10 and arm 20 through a pivot 50. Each arm 15, 20 has an end 30, 35, respectively, that is D-shaped with parallel, sharp serrations on the interior surfaces. When using this device to insert a catheter into a patient, a medical professional will insert his or her fingers into the apertures 2, 3 and open the handles 5, 10, which correspondingly open the arms 15, 20. The health care professional will then close the handles 5, 10, accordingly closing the arms 15, 20, so that the ends 30, 35 grip the catheter. The device 1 is then used to push the catheter through the patient's vocal cords to allow ventilation or to insert the catheter into any other part of the patient's body as deemed necessary by the medical professional.

The device 1 does not allow for guiding of the catheter because the ends 30, 35 must grip the catheter and are used to push the catheter a short distance, which is repeated numerous times so as to advance the catheter. Further, because of the presence of his or hand due to the bent section 60 of the device 1, the medical professional using the device 1 will be blocked from viewing of the patient's vocal cords or other body part into which the catheter will be inserted.

Figure 2:
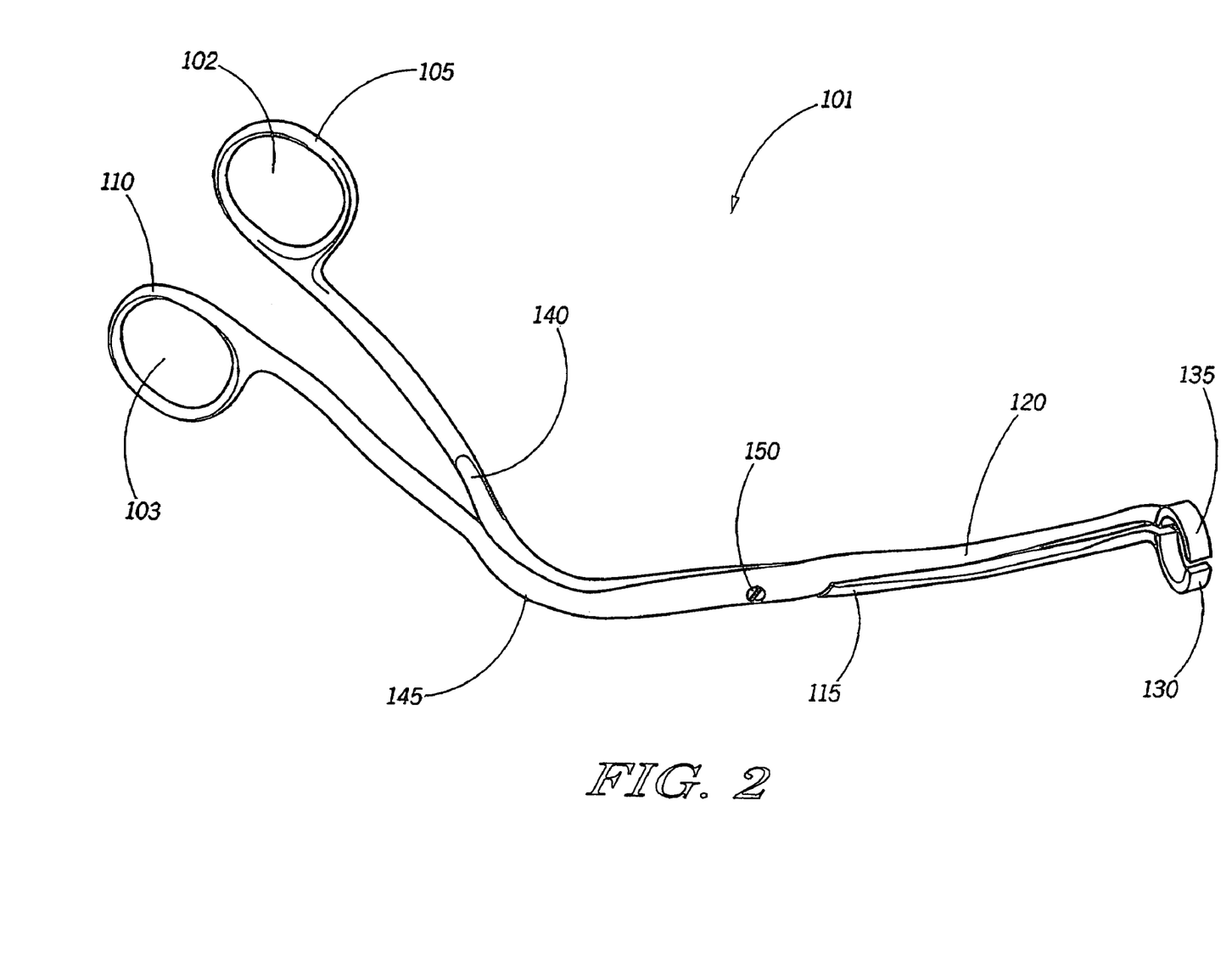
FIG. 2 is a left side elevational view of the implement of the present invention with the arms closed.

The present invention can be more fully understood with reference to FIGS. 2-11, in which like reference numerals designate like items. FIG. 2 depicts the forceps 101, which is an improvement over the device 1 currently in use. The pair of handles 105, 110 of the forceps 101 each defines a gripping section 102, 103, respectively, upon which the medical professional can place his or her fingers to use the forceps 101. Gripping sections 102, 103 can be of any shape. The shape shown is only illustrative. The handles 105, 110 are integrally connected to a pair of arms, 115, 120. The handle 105 and arm 115 is pivotally connected to the handle 110 and arm 120 at a pivot 150. Each arm 115, 120 has an end 130, 135, respectively, that is substantially semicircular in shape; however, the shape of the ends 130, 135 may, within the scope of the invention, be any shape that would allow the ends 130, 135 to form a guide when in the closed position such that a catheter may be easily passed therethrough. When the arms 115, 120 are in the closed position as shown in FIGS. 2 and 4-7, the ends 130, 135 together form a hollow guide adapted to receive and guide the catheter so that the catheter can be advanced through the patient's vocal cords. In the closed position, the interior surface of the hollow guide formed by the ends 130, 135 is preferably slightly larger than 8 mm across, which is slightly larger than the diameter of a standard-sized catheter used for medical purposes today. It is understood that the size of the guide formed by the ends 130, 135 may be varied within the scope of this invention depending upon the diameter of the catheter, including but not limited to catheters that are used in infant patients. All that is required is that the catheter be able to be slid or translated within the guide when the guide is in the closed position.

Figure 3:
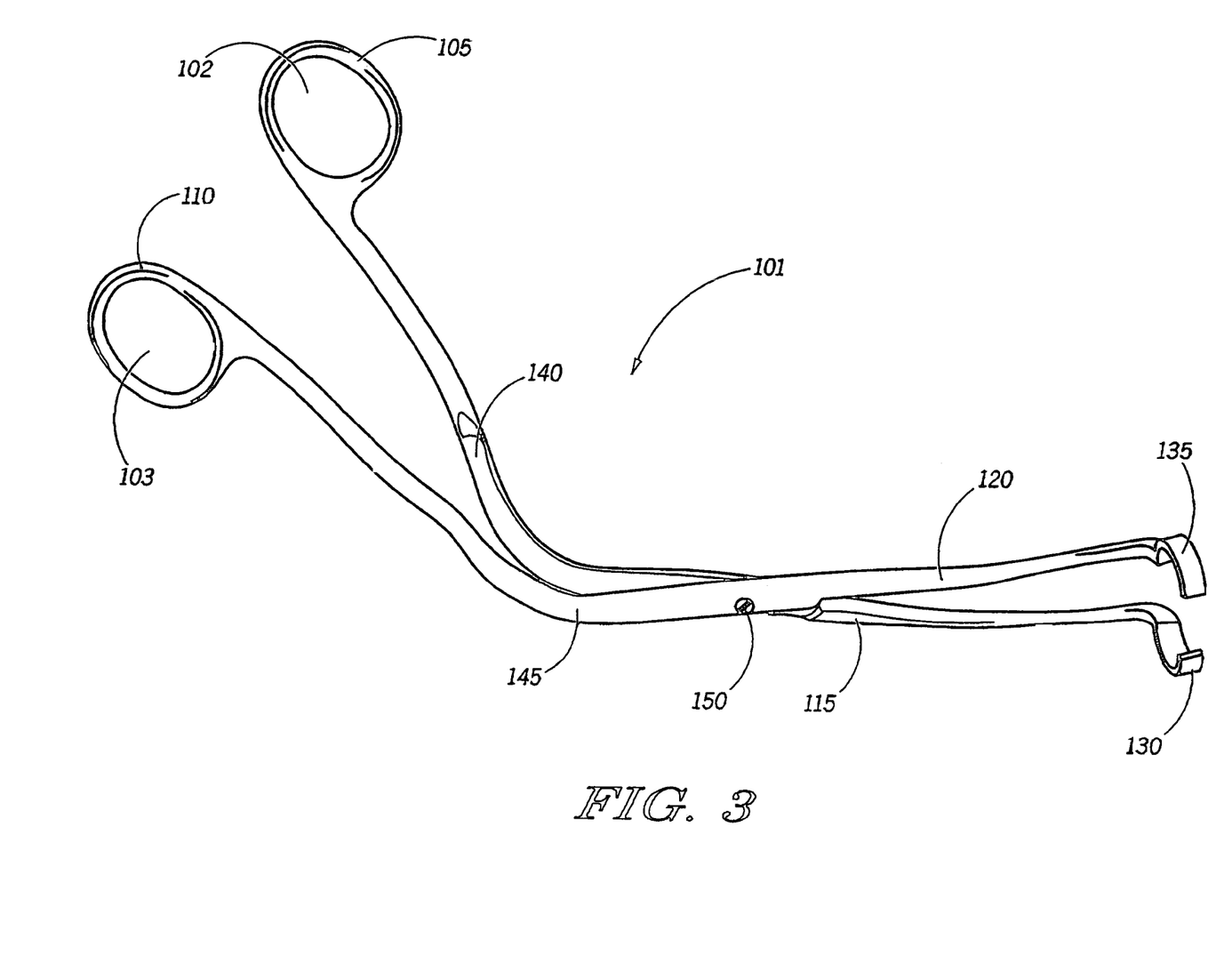
FIG. 3 is a left side elevational view of the implement of FIG. 2 with the arms open.

When using this device to insert a catheter into a patient, a health care professional will insert his or her fingers into the apertures 102, 103 and open the handles 105, 110, which correspondingly open the arms 115, 120. FIG. 3 depicts the forceps 101 in the open position. The catheter is then inserted through the circular aperture defined by the ends 130, 135 of the arms 115, 120. The arms 115, 120 are positioned so that the guide is placed in registry with the patient's glottis (the opening in the vocal cords) so that the catheter can be accurately inserted into the proper location in the patient's body, such as through the patient's vocal cords. The first bend 140 and the second bend 145 allow the medical professional to have an unobstructed view of the patient's vocal cords or other body part into which the catheter is to be inserted. This allows for faster and more accurate insertion of the catheter, without the risk of harm to the patient or damage to the catheter that arises when the medical professional must grip and re-grip the catheter as with currently-available devices, such as the device depicted in FIG. 1.

Figure 4:
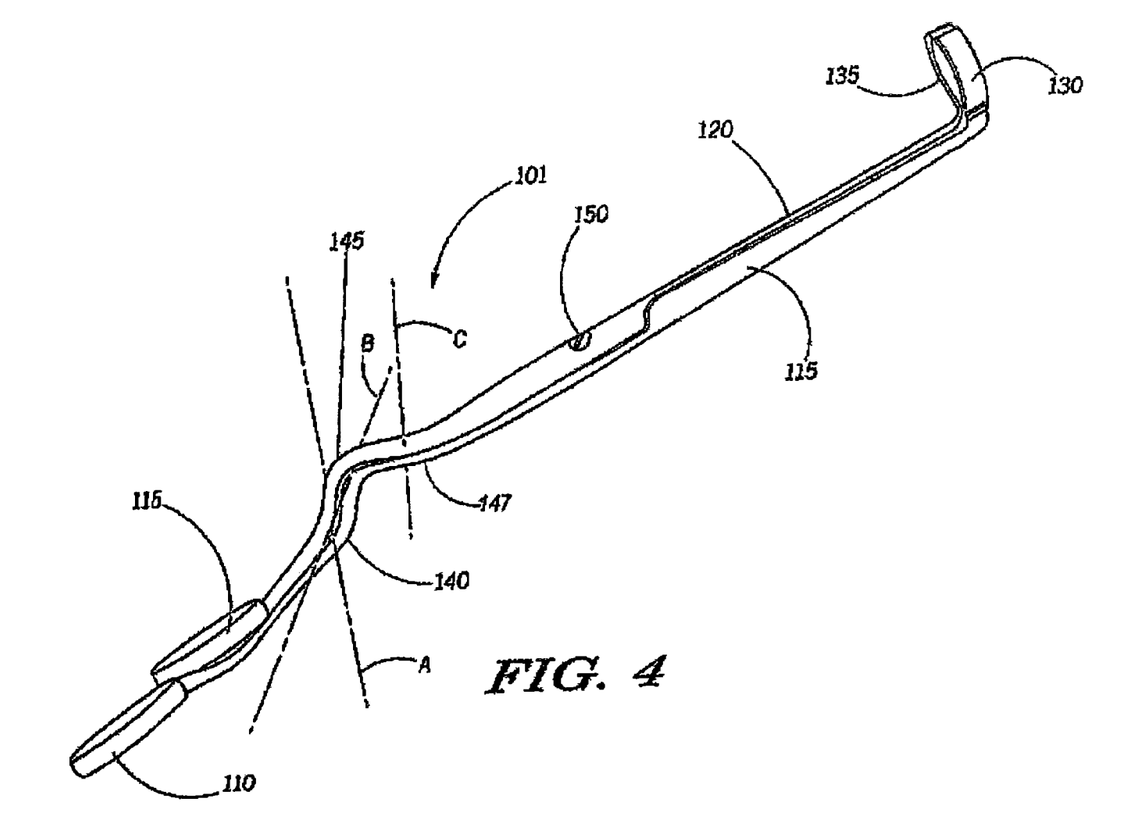
FIG. 4 is a top plan view of FIG. 2.

FIG. 4 depicts the forceps shown in FIG. 2 from the top. The first bend 140, second bend 145, and third bend 147 are clearly visible from this view. The combination of the first bend 140 and second bend 145 provides the medical professional with an unobstructed view of the patient's vocal cords because the user's hand that holds the forceps is off to the side of the mouth while the guide is in registry with the glottis. The third bend 147 contributes to the unobstructed view of the patient's vocal cords. The first bend 140 is bent about an axis A to create an obtuse angle. The second bend 145 is bent about an axis B to create an obtuse angle that is preferably, but not necessarily, approximately 120°. The third bend 147 is bent about an axis C to create an obtuse angle that is preferably, but not necessarily, approximately 150°.

Figure 5:
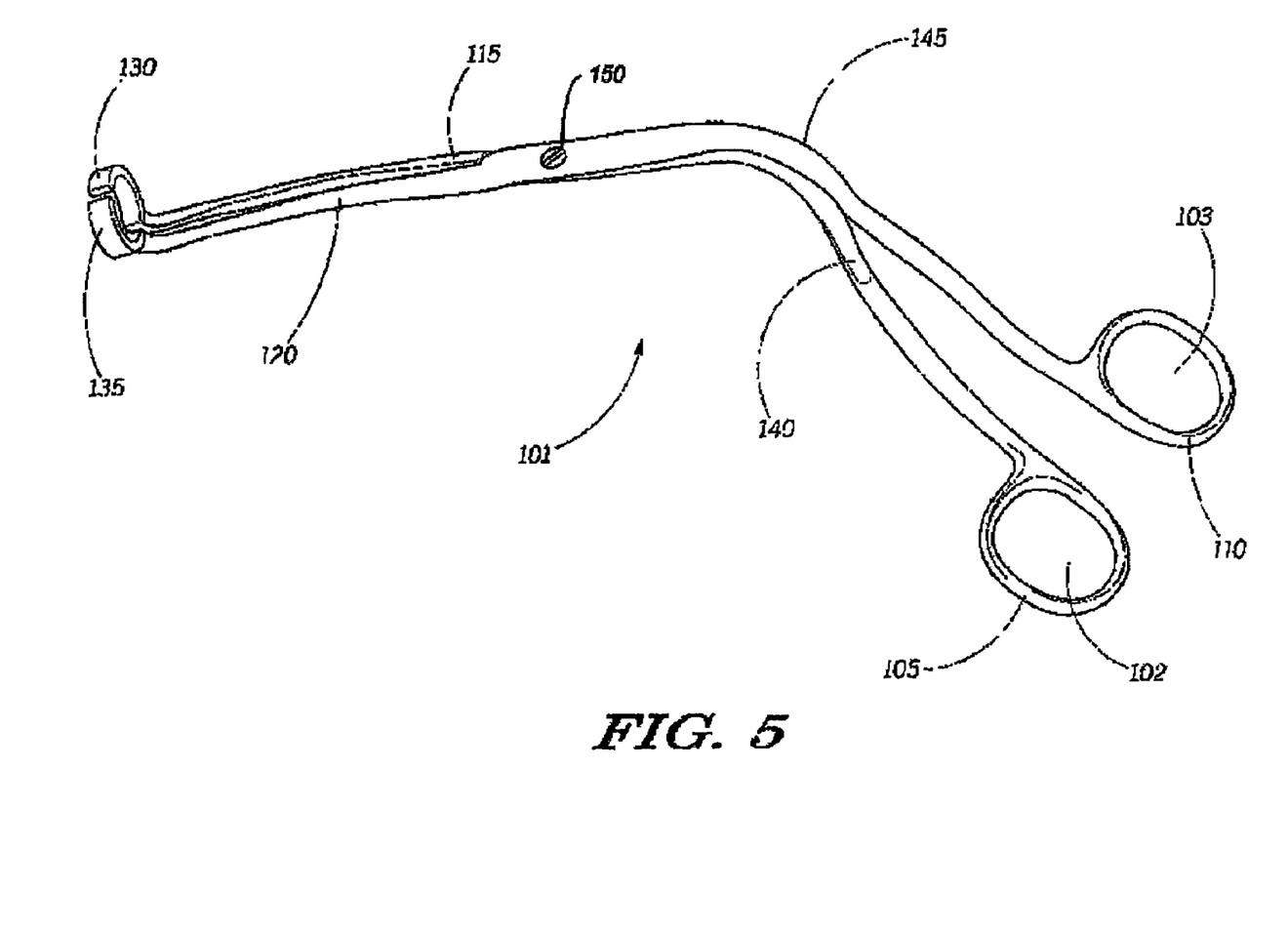
FIG. 5 is a right side elevational view of FIG. 2.

FIG. 5 is a right side view of the forceps shown in FIG. 2. The arms 115, 120 and the ends 130, 135 are smooth, having no sharp edges or teeth that could harm a patient's tissue or damage the balloon portion of a catheter.

Figure 6:
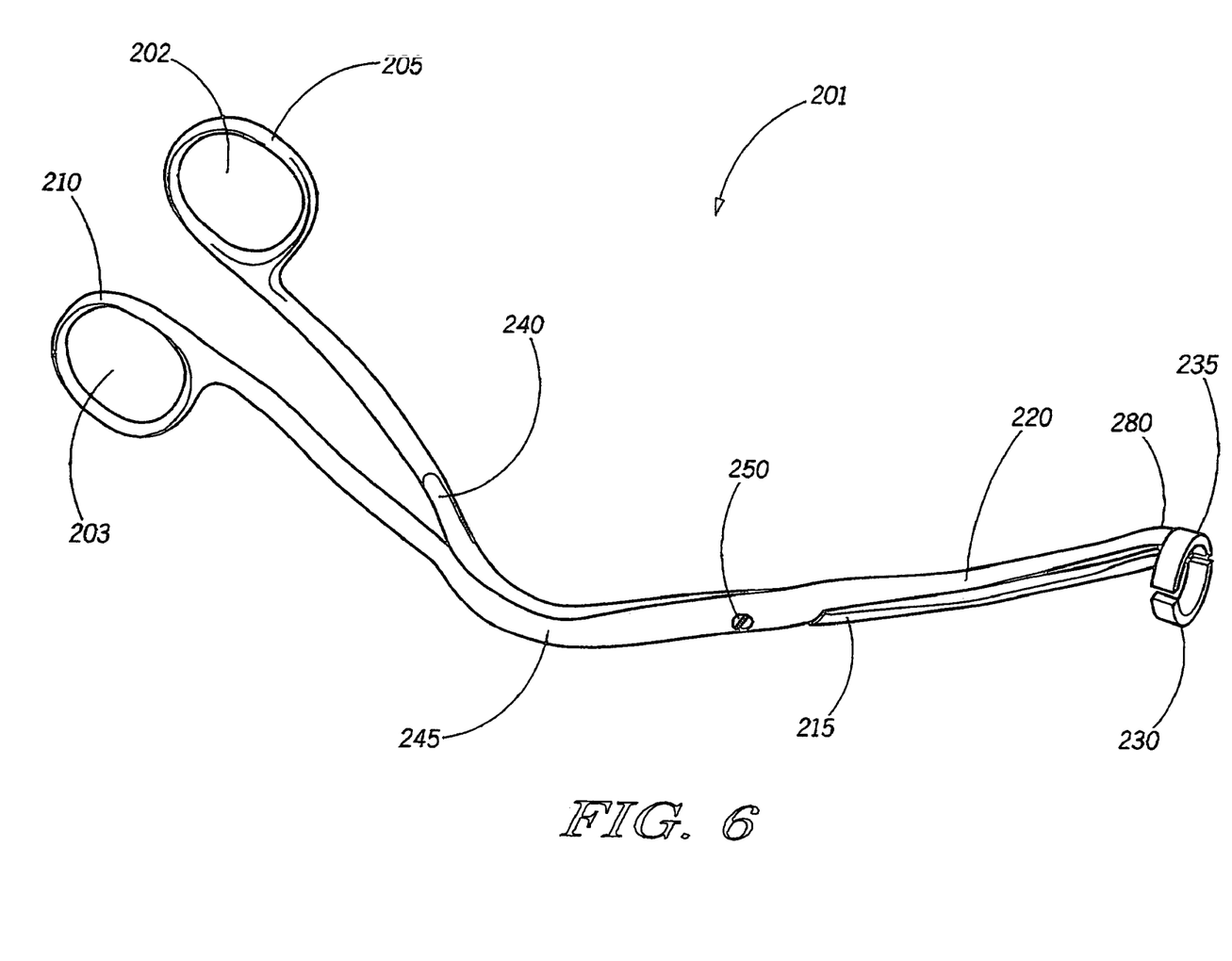
FIG. 6 is a left side elevational view of an alternative embodiment of the present invention.

An alternative embodiment of the forceps 201 is depicted in FIG. 6. The pair of handles 205, 210 of the forceps 201 each defines an aperture 202, 203 through which the medical professional can insert his or her fingers to use the forceps 201. The handles 205, 210 are integrally connected to a pair of arms 215, 220. The handle 205 and arm 215 is pivotally connected to the handle 210 and arm 220 at a pivot 250. Each arm 215, 220 has an end 230, 235, respectively, that is substantially semicircular in shape; however, the shape of the ends 230, 235 may, within the scope of the invention, be any shape that would allow the ends 230, 235 to form a guide when in the closed position such that a catheter may be easily passed therethrough. When the arms 215, 220 are in the closed position as shown in FIG. 6, the ends 230, 235 together form a hollow guide adapted to receive and guide the catheter so that the catheter can be advanced into the patient's glottis. In the preferred embodiment, when the arms are in their closed position, the interior surface of the hollow guide formed by the ends 230, 235 is preferably slightly larger than 8 mm across, which is slightly larger than the diameter of a standard-sized catheter used for medical purposes today. It is understood that the size of the guide formed by the ends 230, 235 may be varied within the scope of this invention depending upon the diameter of the catheter, including but not limited to catheters that are used in infant patients.

The forceps 201 has a first bend 240 and a second bend 245 that together allow the medical professional to have an unobstructed view of the patient's glottis and vocal cords or other body part into which the catheter is to be inserted. The difference between the forceps 101 and the forceps 201 is that the forceps 201 has a fourth bend 280 located immediately before the ends 230, 235. The fourth bend 280 rotates the ends 230, 235 approximately fifteen degrees clockwise from their standard position, although a greater or lesser magnitude of bend may be desirable as will occur to the person of skill in the art. Also, the bend 280 may be as shown (acute) or may rotate the ends 230, 235 in the opposite direction, creating an obtuse angle. The angle of insertion of a catheter through the ends 230, 235 is changed by the fourth bend 280, allowing for an easier insertion in patients that have a shorter neck, such as children or small adults. It is understood that the degree of the angle of the fourth bend 280 may vary according to the needs of a particular situation within the scope of this invention.

Figure 7:
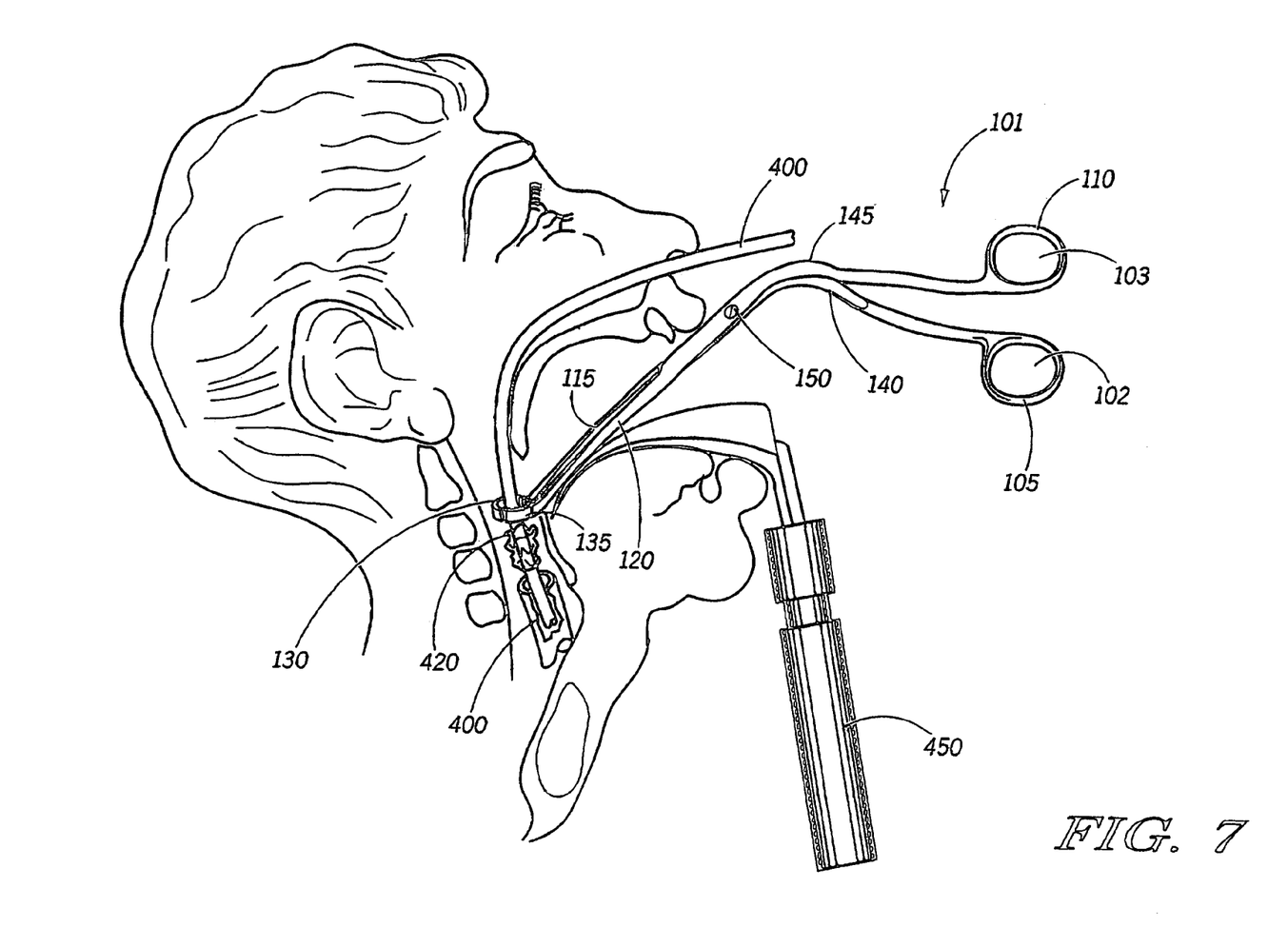
FIG. 7 is a side cutaway view illustrating the use of the present invention in a patient.
Figure 8:
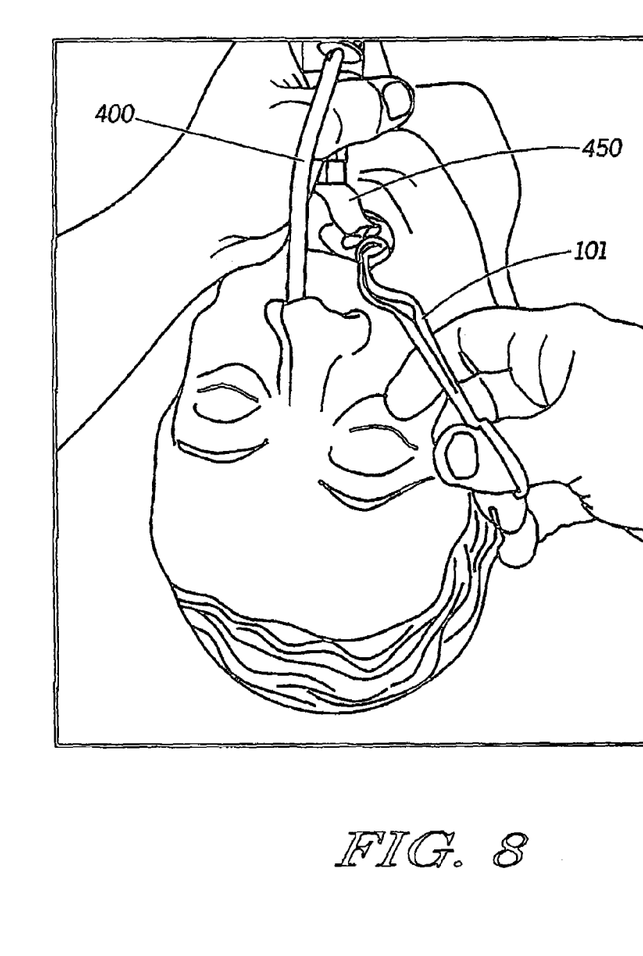
FIG. 8 is a diagrammatic representation showing the use of the present invention in a patient.
Figure 9:
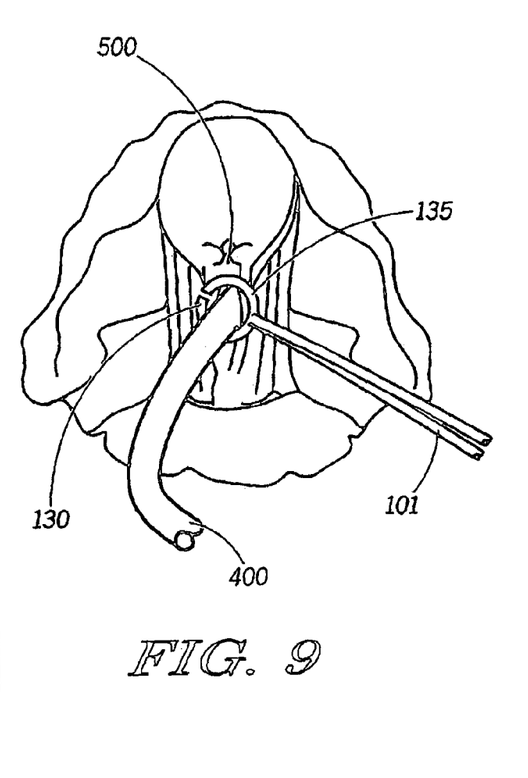
FIG. 9 is a plan view showing the invention being used in a patient.

FIGS. 7 through 9 illustrate the use of the forceps 101 and a laryngoscope 450 in a patient. Nasal endotracheal intubation is illustrated in FIG. 7, wherein a ventilation tube 400 is inserted into the patient's nose and passed through the patient's sinus cavity into the back of the patient's throat. A laryngoscope 450 is used to secure the patient's tongue and provide light to the patient's throat. As the medical professional holds the forceps 101 in registry with the patient's glottis 500, a medical assistant, such as a nurse, will advance the ventilation tube 400 through the ends 130, 135 of the forceps 101 and through the patient's glottis 500. After being properly located, the balloon portion 420 of the ventilation tube 400 is inflated to secure a seal and allow for proper ventilation.

Figure 10:
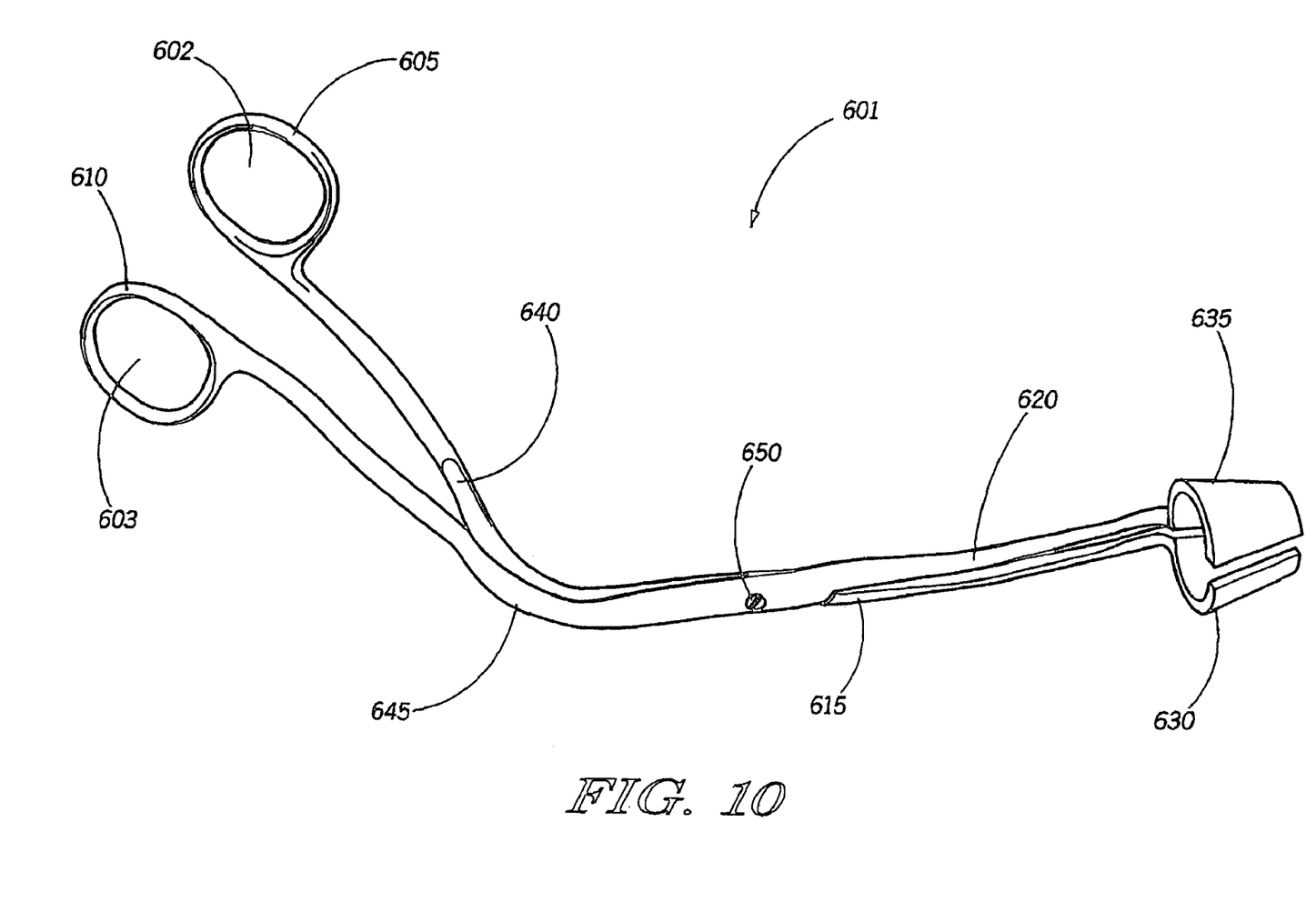
FIG. 10 is a left side elevational view of a further a further embodiment of the invention.

An alternative embodiment of the forceps 601 is depicted in FIG. 10. The pair of handles 605, 610 of the forceps 601 each defines an aperture 602, 603 through which a medical professional can insert his or her fingers to use the forceps 601. The handles 605, 610 are integrally connected to a pair of arms 615, 620, respectively. The handle 605 and arm 615 is pivotally connected to the handle 610 and arm 620 at pivot 650. Each arm 615, 620 has an end 630, 635, respectively, that is substantially shaped as half of a cone (or, alternatively, as half of a cylinder); when the arms 615, 620 are in the closed position as shown in FIG. 10, the ends 630, 635 together form a cone-shaped (or cylindrically-shaped) guide adapted to receive and guide a catheter so that the catheter can be advanced into the patient's glottis. The diameter of the cone-shaped ends 630, 635, when closed, is preferably slightly larger than 8 mm across at its narrowest point. The portion of the ends 630, 635 that is closer to the handles 605, 610 preferably has a diameter larger than 8 mm. In the closed position, the interior surface of the hollow guide formed by the cone-shaped ends 630, 635 acts as a funnel of sorts to allow the medical professional to more easily guide the end of a catheter through the cone-shaped ends 630, 635. It is understood that the size of the guide formed by the ends 630, 635 may be varied within the scope of this invention depending upon the diameter of the catheter, including but not limited to catheters that are used in infant patients. The forceps 601 has a first bend 640 and a second bend 645 that together allow the medical professional to have an unobstructed view of the patient's glottis and vocal cords or other part into which the catheter is to be inserted.

Figures 11, 12, 13:
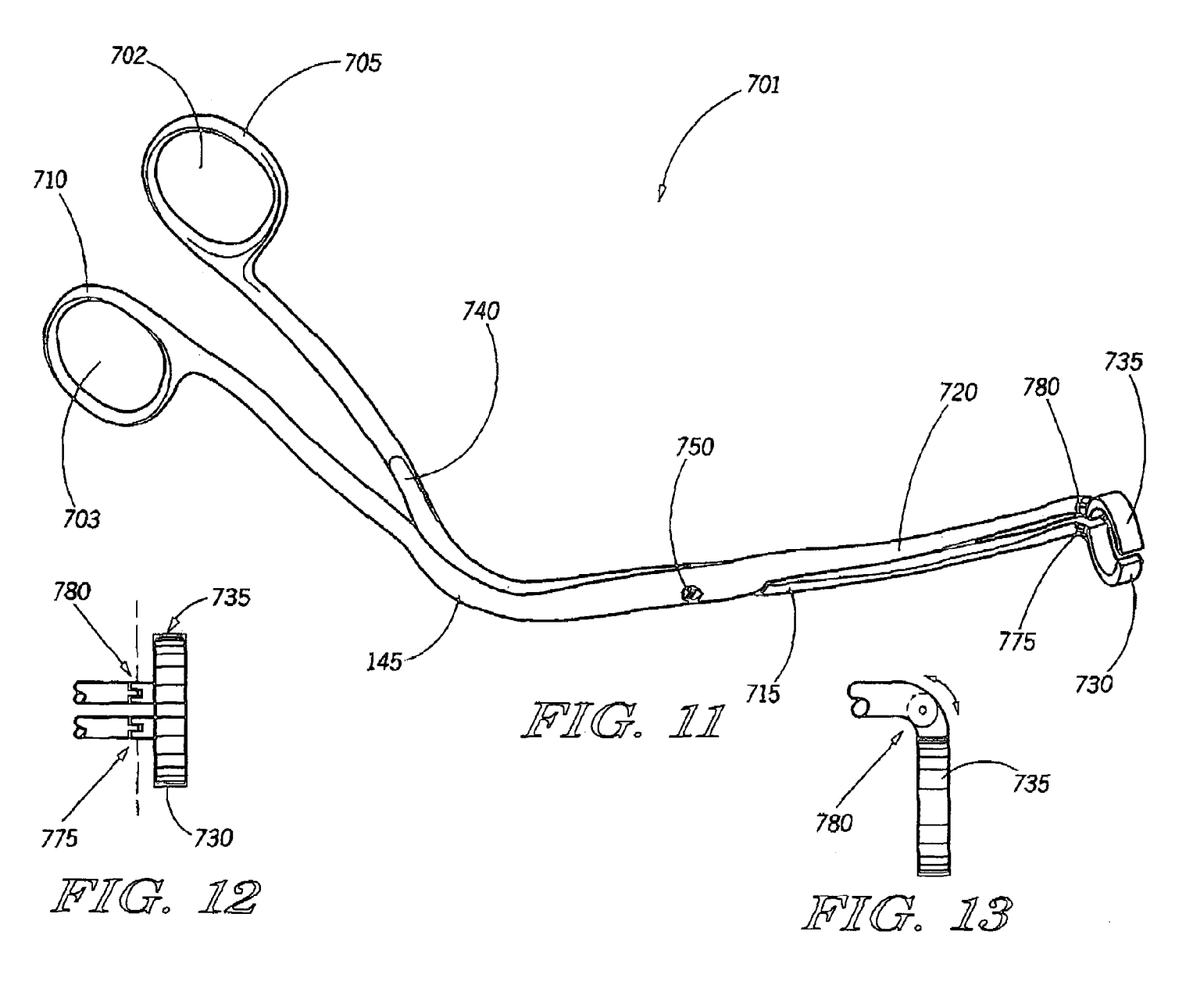
FIG. 11 is a left side elevational view of a still further embodiment of the invention.
FIG. 12 is an enlarged detail of the distal end of the device of the embodiment of FIG. 11.
FIG. 13 is plan view of the distal end shown in FIG. 12.

Another alternative embodiment of the forceps 701 is depicted in FIGS. 11-13. The pair of handles 705, 710 of the forceps 701 each defines an aperture 702, 703 through which the medical professional can insert his or her fingers to use the forceps 701. The handles 705, 710 are integrally connected to a pair of arms 715, 720, respectively. The handle 705 and arm 715 is pivotally connected to the handle 710 and arm 720 at a pivot 750. Each arm 715, 720 has an end 730, 735, respectively, that is substantially semi-circular in shape. However, the shape of the ends 730, 735 may, within the scope of the invention, be any shape that would allow the ends 730, 735 to form a guide when in the closed position such that a catheter may be easily passed therethrough. When the arms 715, 720 are in the closed position as shown in FIG. 11, the ends 730, 735 together form a hollow guide adapted to receive and guide the catheter so that the catheter can be advanced into the patient's glottis. In the closed position, the interior surface of the hollow guide formed by the ends 730, 735 is preferably slightly larger than 8mm across, which is slightly larger than the diameter of a standard-sized catheter used for medical purposes today. It is understood that the size of the guide formed by the ends 730, 735 may be varied within the scope of this invention depending upon the diameter of the catheter, including but not limited to catheters that are used in infant patients.

The forceps 701 has a first bend 740 and a second bend 745 that together allow the medical professional to have an unobstructed view of the patient's glottis and vocal cords or other body parts into which the catheter is to be inserted. Ends 730, 735 are pivotally connected to arms 715, 720, respectively, by joints 775, 780. The joints 775, 780 are preferably located about the same axis, as indicated in FIG. 12. The ends 730, 735 are permitted to rotate about the joints 775, 780 to allow for immediate adaptation of the forceps 701 to the angle of insertion required by a patient's body. Any suitable means may be employed for releasably retaining the ends 730, 735 in any desired angular position relative to arms 715, 720, such as opposed serrations or teeth (not shown). Other retention structure will be apparent to those of skill in the art. However, retention structure need not necessarily be used. In this manner, the medical professional using the forceps 701 is not required to change the instrument he or she is using upon discovering that a different angle of insertion of a catheter is required by a particular patient's anatomy.

Benefits, other advantages, and solutions to problems have been described above with regard to specific embodiments of the present invention. However, the benefits, advantages, solutions to problems, and any element(s) that may cause or result in such benefits, advantages, or solutions to become more pronounced are not to be construed as a critical, required, or essential feature or element of any or all the claims. As used herein and in the appended claims, the terms "comprises," "comprising" or any other variation thereof is intended to refer to a non-exclusive inclusion, such that a process, method, apparatus, or article of manufacture that comprises a list of elements does not include only those elements in the list, but may include other elements not expressly listed or inherent to such process, method, apparatus, or article of manufacture.

I claim:

1. A naso-endotracheal tube guiding device for inserting a naso-endotracheal tube into a patient, the naso-enclotracheal tube guiding device comprising:

a pair of arms pivotally connected for relative movement between a first, opened position and a second, closed position;

each arm comprising a distal end and a proximal end;

the distal end of the first arm defining a first tube guide half section that combines with a second tube guide half section defined by the distal end of the second arm to form a tube guide when the arms are in the closed position, the tube guide defining an inwardly facing surface which is sized and shaped so that it does not make gripping engagement with the tube so as to permit free coaxial movement of the tube within the guide;

each arm defining a first bend and a second bend located between the pivot and the proximal ends of each arm, the arms along each of the first and second bends being substantially parallel with each other, and each arm further defining a third bend located between the second bend and the proximal end of the arms, the arms along the third bend being substantially parallel with each other, the bends oriented in such a way that the proximal ends of each arm do not visually interfere with the distal ends when the distal ends of each arm are placed inside the patient's pharynx, allowing an unobstructed view of the patient's vocal cords;

the first, second and third bends lying in an area of the device which is substantially equidistant between the pivot and the proximal end of the device;

the angle formed by the second bend is substantially 120°;

the angle formed by the third bend is substantially 150°;

the first bend lies about a first axis;

the second bend lies about a second axis;

the third bend lies about a third axis; and the first, second, and third axes are non-parallel.

2. The naso-endotracheal tube guiding device of claim 1, wherein the tube guide is substantially cone-shaped when the arms are in the closed position.

3. The naso-endoiracheal tube guiding device of claim 1, further comprising:

the first tube guide half section being rotatably connected to the distal end of the first arm along an axis of rotation which is substantially perpendicular to the first arm; and the second tube guide half section being rotatably connected to the distal end of the second arm along an axis of rotation which is substantially perpendicular to the second arm.

4. The naso-endotracheal tube guiding device of claim 1, wherein:

the first tube guide half section lies in a plane which is substantially perpendicular to the first arm; and the second tube guide half section lies in a plane which is substantially perpendicular to the second arm.

5. The naso-endotracheal tube guiding device of claim 1, wherein each bend forms an obtuse angle between adjacent sections of the respective arm on either side of the bend.

6. A naso-endotracheal tube guiding device for inserting a naso-endotracheal tube into a patient, the naso-endotracheal tube guiding device comprising:

a pair of arms connected by a hinge to pivot between a first, open position and a second, closed position;

each arm comprising a distal end and a proximal end;

each distal end defining a tube guide section that forms a tube guide when the arms are in their closed position, the tube guide defining an inwardly facing surface which is sized and shaped so that it does not make gripping engagement with the tube so as to permit free coaxial movement of the tube within the guide;

each arm defining a first bend and a second bend located between the hinge and the proximal ends of each arm;

each arm further defining a third bend located between the second bend and the proximal end of the arms;

wherein the first, second and third bends lie in an area of the device which is substantially equidistant between the pivot and the proximal end of the device;

wherein the arms run parallel to each other along the first, second, and third bends;

the first bend lies about a first axis;

the second bend lies about a second axis;

the third bend lies about a third axis; and the first, second, and third axes are non-parallel.

7. The naso-endotracheal tube guiding device of claim 6, wherein the tube guide is substantially cone-shaped when the arms are in the closed position.

8. The naso-endotracheal tube guiding device of claim 6, further comprising:

each tube guide section being rotatably connected to the distal end of the respective arm to which it is attached, along an axis of rotation which is substantially perpendicular to the respective arm to which it is attached.

9. The naso-endotracheal tube guiding device of claim 6, wherein:

each tube guide section lies in a plane which is substantially perpendicular to the distal end of the respective arm to which it is attached.

10. The naso-endotracheal tube guiding device of claim 6, wherein each bend forms an obtuse angle between adjacent sections of the respective arm on either side of the bend.

11. A naso-endotracheal tube guiding device for inserting a naso-endotracheal tube into a patient, the naso-endotracheal tube guiding device comprising;

a pair of arms pivotally connected for relative movement between a first, opened position and a second, closed position;

each arm comprising a distal end and a proximal end, the distal end of the first arm defining a first tube guide half section that combines with a second tube guide half section defined by the distal end of the second arm to form a tube guide when the arms are in the closed position, the tube guide defining an inwardly facing surface which is sized and shaped so that it does not make gripping engagement with the tube so as to permit free coaxial movement of the tube within the guide;

each tube guide half section lying in a plane which is substantially perpendicular to the respective arm to which it is attached;

each arm defining a first bend and a second bend located between the pivot and the proximal ends of each arm, and a third bend located between the second bend and the proximal end of the arms, the bends oriented in such a way that the proximal ends of each arm do not visually interfere with the distal ends when the distal ends of each arm are placed inside the patient's pharynx, allowing an unobstructed view of the patient's vocal cords;

wherein the first, second and third bends lie in an area of the device which is substantially equidistant between the pivot end and the proximal end of each arm, and wherein the arms run parallel to each other along the first, second, and third bends; and each bend forming an obtuse angle between adjacent sections of the respective arm on either side of the bend, wherein the angle formed by the second bend is substantially 120° and the angle formed by the third bend is substantially 150°;

the first bend lies about a first axis;

the second bend lies about a second axis;

the third bend lies about a third axis; and the first, second, and third axes are non-parallel.

* * * * *